US005123409A

United States Patent [19]

Sheffield et al.

[11] Patent Number: 5,123,409

[45] Date of Patent: Jun. 23, 1992

[54] EMERGENCY OXYGEN SUPPLY SYSTEM

[75] Inventors: David P. Sheffield, Wyndmoor; Richard J. Boyles, Harleysville; Charles A. McMenamy, Easton, all of Pa.

[73] Assignee: Scott Specialty Gases, Inc., Plumsteadville, Pa.

[21] Appl. No.: 533,602

[22] Filed: Jun. 5, 1990

[51] Int. Cl.[5] .................. A61M 16/00; A62B 7/00; A62B 9/02

[52] U.S. Cl. .................. 128/204.18; 128/205.24

[58] Field of Search .................. 128/204.18, 202.27, 128/205.22, 205.21, 205.24, 205.25; 220/581, 582; 137/376; 206/0.6

[56] References Cited

U.S. PATENT DOCUMENTS

| | | | |
|---|---|---|---|
| Re. 28,334 | 2/1975 | Cranage | 137/360 |
| 2,138,845 | 12/1938 | Erikson | 128/203.24 |
| 2,329,289 | 9/1943 | Morehouse | 128/205.24 |
| 2,733,042 | 1/1956 | Culbertson | 128/205.24 |
| 2,852,023 | 9/1958 | Hamilton et al. | 128/205.12 |
| 3,229,851 | 1/1966 | Horwitt et al. | 128/205.22 |
| 3,491,752 | 1/1970 | Cowley | 128/205.22 |
| 3,791,403 | 2/1974 | Folkerth | 128/204.18 |
| 4,044,712 | 8/1977 | Goodman et al. | 116/142 FP |
| 4,233,970 | 11/1980 | Kranz | 128/201.28 |
| 4,475,664 | 10/1984 | Mackal | 222/5 |
| 4,550,861 | 11/1985 | Fay | 222/78 |
| 4,603,833 | 8/1986 | Christianson | 251/94 |
| 4,620,598 | 11/1986 | Reeder | 169/30 |
| 4,798,203 | 1/1989 | Bartos | 128/205.22 |
| 4,802,472 | 2/1989 | Jung | 128/204.18 |
| 4,805,802 | 2/1989 | MacKendrick et al. | 222/5 |
| 4,944,292 | 7/1990 | Gaeke et al. | 128/204.18 |

FOREIGN PATENT DOCUMENTS

| | | | |
|---|---|---|---|
| 670380 | 9/1963 | Canada | 128/202.27 |

*Primary Examiner*—Edgar S. Burr
*Assistant Examiner*—Kimberly L. Asher
*Attorney, Agent, or Firm*—Dykema Gossett

[57] ABSTRACT

An emergency oxygen supply system is disclosed in which a oxygen tank and valve body are mounted on a bracket including a pin maintaining a valve within the valve body in a position blocking fluid flow from the tank to an oxygen mask. Flow of oxygen from the oxygen tank to the oxygen mask is automatically actuated upon removal of the tank and valve body from the bracket, since the pin remains with the bracket, and the valve no longer blocks fluid flow. The valve also provides pressure regulation to prevent overly high pressures from passing from the oxygen tank to the oxygen mask.

14 Claims, 2 Drawing Sheets

EMERGENCY OXYGEN SUPPLY SYSTEM

BACKGROUND OF THE INVENTION

This application relates to emergency oxygen supply systems, and more particularly to a system that is automatically actuated to supply oxygen when removed from a storage position.

Emergency oxygen supply systems are known in which oxygen flow from an oxygen tank to an oxygen mask is blocked by a valve maintained in a closed position by a pin. Upon removal of the pin, the valve moves to an open position and oxygen may flow from the tank to the mask. A system as described above is disclosed in U.S. Pat. No. 4,802,472.

Other prior art oxygen supply systems have similar pins that can be pulled to force a perforator into a seal on an oxygen tank. Once the seal is perforated, oxygen can flow from the tank to an oxygen supply point, such as a mask. Systems as described above are disclosed in U.S. Pat. Nos. 2,852,023 and 4,805,802.

These prior art systems are stored in locations where an emergency oxygen supply may become necessary, and the tanks must maintain an adequate quantity of oxygen over a long period of time, thus, flow is normally blocked. At the same time, it is essential in an emergency situation that the flow from an oxygen tank to the mask be actuated quickly. The pins disclosed in the prior art have attempted to provide this quick actuation. The prior art systems have been deficient, however, in some respects.

One problem with the prior art systems is that the emergency actuation of oxygen flow normally requires a two-step procedure. The systems are maintained in some storage position; an operator must first remove the system from this storage position, and then locate and remove the pin to actuate flow. Situations which require an emergency oxygen supply do not lend themselves to careful study of a system in order to actuate it. Prior art systems that require removal from a storage position, then searching for a pin that must be removed, require excessive time. In a situation where emergency flow of oxygen is necessary, the elimination of one of these two steps would be desirable.

Most oxygen supply systems also require some sort of regulator valve to prevent overly high pressures from reaching an oxygen supply mask. In the prior art systems the valves which block flow from the tank to the mask do not also regulate the pressure supplied to the mask. It would be desirable, from a simplicity of manufacture standpoint, as well as to remove unnecessary obstructions in the flow path, to achieve both of these valving functions with a single valve.

It is therefore an object of the present invention to disclose an emergency oxygen supply system in which the flow of oxygen from a tank to a mask is actuated with a one-step procedure. In addition, it is an object of the present invention to disclose an emergency oxygen supply system in which the flow of oxygen from a tank to a mask is selectively blocked, and the pressure supplied from the tank to the mask is also regulated, through a single valve.

SUMMARY OF THE INVENTION

A disclosed embodiment of the present invention includes a bracket for mounting an oxygen tank and a valve body in a storage position. A valve within the valve body is biased towards a position allowing flow from the tank to a oxygen mask, however a portion of the bracket maintains this valve in a position blocking flow. The oxygen tank and valve body may be removed from the bracket, and the bracket portion will no longer maintain the valve in a position blocking flow. The valve is then biased to a position allowing flow from the tank to the mask. Thus, in one-step, the removal of the oxygen tank and valve body from the storage position on the bracket, flow is actuated to supply oxygen from the oxygen tank to an oxygen mask.

In one preferred embodiment of the present invention, the bracket portion which normally maintains the valve in a position blocking flow is a hook member, over which a ring is received. The ring is attached to a pin and the valve body has an aperture to receive this pin. The valve in the valve body has a valve seal at a first end which may engage a valve seat to block flow from the oxygen tank to the oxygen mask. Spring means bias the valve upwardly into the aperture to remove the valve seal from the valve seat and allow flow from the oxygen tank to the oxygen mask. When the pin is received in the aperture, it forces the valve against the spring bias to engage the valve seal with the valve seat, and block flow from the oxygen tank to the oxygen mask.

When emergency oxygen is desired, the oxygen tank and valve body are removed from the bracket, the hook retains the ring with the bracket, and the pin is removed from the aperture. The valve is biased upwardly into the aperture and the valve seal moves away from the valve seat, thus actuating flow of oxygen from the oxygen tank to the oxygen mask.

In a most preferred embodiment of the present invention, the valve includes two pistons, with a first regulator piston receiving the valve seal and being spring biased upwardly away from a valve seat, and a second shut-off piston being spring biased away from the regulator piston upwardly into the aperture. Once the pin has been removed from the aperture, and the valve has moved to the position allowing flow, the regulator piston regulates the pressure of oxygen being sent to the oxygen mask. The regulator piston has a passage that taps a portion of the oxygen being supplied to the mask to a first regulator piston face, where it acts in opposition to the spring bias maintaining the regulator piston and valve seal away from the valve seat. If the oxygen pressure becomes overly high, the pressure on the first regulator piston face overcomes (he spring bias and the valve seal is moved towards the valve seat, impeding flow and preventing any overly high pressures from reaching the oxygen mask.

In a most preferred embodiment, the bracket portion includes an integral pin which is received in the aperture in the valve body. When the tank and valve body are removed from the bracket, the pin is pulled out of the aperture and the valve moves to the position allowing flow.

As an additional feature, a second pin may be maintained in the vicinity of the bracket. When it is necessary to transport the emergency oxygen supply system to a remote location, the tank and valve body are removed from the bracket, and the second pin is inserted in the aperture, moving the valve to the position blocking flow. The system can then be transported to the remote location, where the second pin is removed from the aperture to allow flow.

Preferably, the pin has a ramped portion initially inserted into the aperture, and the valve has a ball member at the end which extends into the aperture. When the pin is initially moved into the aperture, the ramped portion engages the ball and guides it outwardly of the aperture.

These and other objects and features of the present invention can be best understood from the following specification and drawings, of which the following is a brief description.

DETAILED DESCRIPTION OF DISCLOSED EMBODIMENTS OF THE INVENTION

Figure 1:
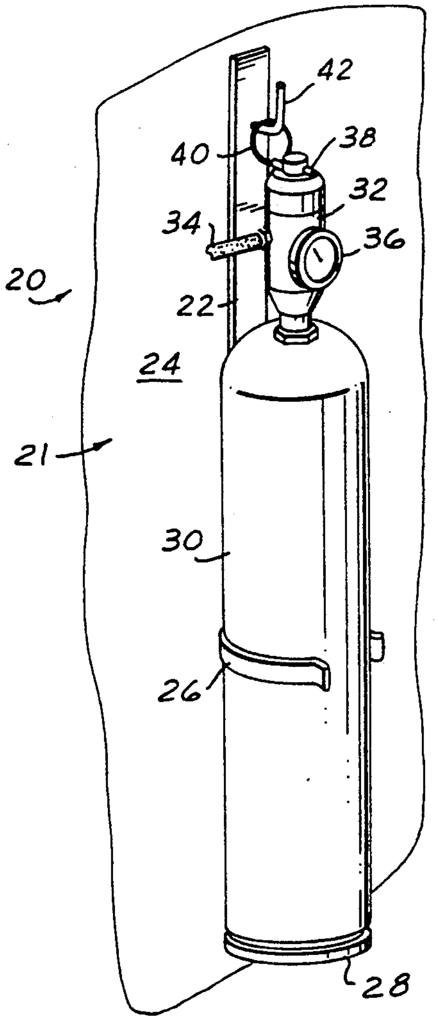
FIG. 1 is a perspective view showing an emergency oxygen supply system in a storage position.

FIG. 1 shows storage position 20 of emergency oxygen supply system 21. Bracket 22 is connected to wall 24 and has center clip 26 and lower support platform 28 to mount a pressurized oxygen tank 30. Valve body 32 is mounted to oxygen tank 30 and is connected by oxygen tube 34 to an oxygen mask, which is not illustrated. Pin 38 extends through valve body 32 and is connected to ring 40, which is received over hook 42 on bracket 22. When system 21 is in storage position 20, pin 38 maintains a valve within valve body 32 is a position blocking flow from oxygen tank 30 to an oxygen mask, through oxygen tube 34. System 21 may thus be stored for a relatively long period of time without losing the pressure within tank 30. This pressure is monitored with pressure gauge 36 to ensure that an adequate supply of oxygen is available should an emergency occur.

Figure 2:
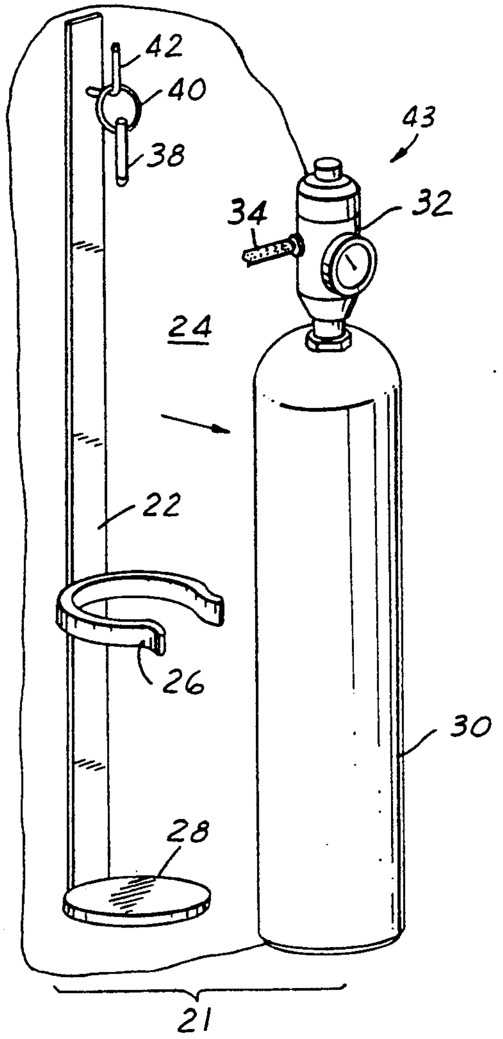
FIG. 2 is a view similar to FIG. 1 but showing the emergency oxygen supply system in a use position.

Emergency oxygen supply system 21 is illustrated in FIG. 2 having been moved out of storage position 20 to an oxygen supply, or use position 43. In use position 43, tank 30 and valve body 32 are removed from bracket 22, with center clip 26 moving resiliently outwardly to allow tank 30 to pass outwardly of bracket 22. Hook 42 retains ring 40 on bracket 22, and pin 38 is removed from valve body 32. Once pin 38 is removed from valve body 32, the valve moves to a position allowing oxygen flow from oxygen tank 30 to oxygen tube 34. Thus, by the single step of removing oxygen tank 30 and valve body 32 from bracket 22, the flow of oxygen to an oxygen mask is automatically actuated.

Figure 3:
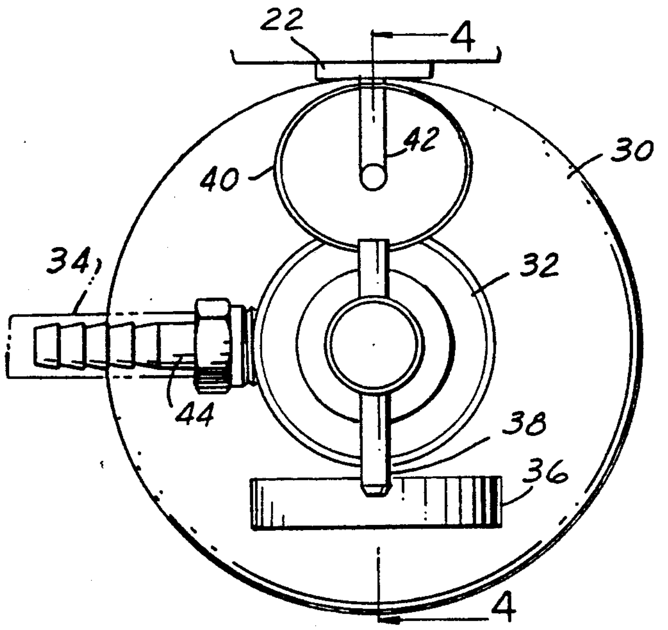
FIG. 3 is a top view of the system illustrated in FIG. 1.

FIG. 3 is a top view of storage position 20, with oxygen tank 30 mounted to bracket 22, and ring 40 hooked over hook 42. Pin 38 extends through valve body 32, and a valve within valve body 32 blocks flow of oxygen from oxygen tank 30, through outlet nipple 44 and into oxygen tube 34.

Figure 4:
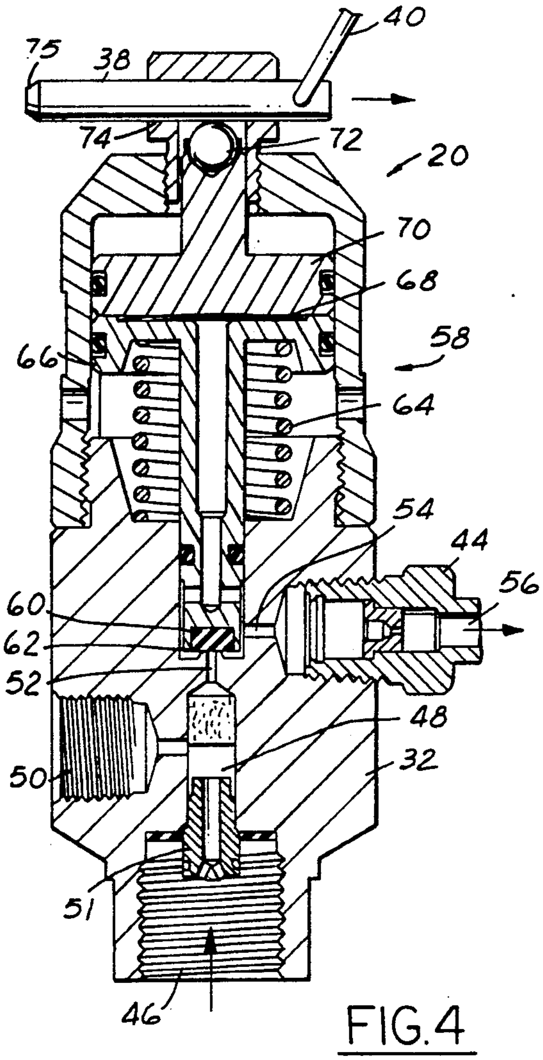
FIG. 4 is a cross-sectional view along lines 4—4 as shown in FIG. 3, showing the system in its flow-preventing condition.

FIG. 4 is a cross-sectional view generally along lines 4—4 as illustrated in FIG. 3, and shows valve body 32 in storage position 20. For purposes of fully explaining the invention, outlet nipple 44 is illustrated rotated 90 degrees from its actual position, which is shown in FIG. 3. Cylinder connection passage 46 communicates valve body 32 to oxygen tank 30 and leads into chamber 48, which is connected to line 50, leading to pressure gauge 36. Pusher pin 51 actuates a valve, such as Schroeder valve in oxygen tank 30 to supply oxygen to chamber 48. Oxygen inlet passage 52 leads to outlet passage 54, which is connected to line 56 in outlet nipple 44.

The previously discussed valve, shut-off pressure regulator valve 58, has valve seal 60 at a lower end seated on valve seat 62, and blocking flow from inlet passage 52 to outlet passage 54. Spring 64 biases first regulator piston 66 upwardly to remove valve seal 60 from valve seat 62. Spring 68, which is preferably a Belleville spring, biases shut-off piston 70 upwardly away from regulator piston 66. Ball 72 is disposed at an upper portion of shut-off piston 70, and aperture 74 is formed in an upper portion of valve body 32 to receive pin 38. Pin 38 forces ball 72 downwardly against the force of spring 68, which in turn forces regulator piston 66 downwardly against the force of spring 64, such that valve seal 60 is maintained in sealing engagement with valve seat 62, blocking flow of oxygen from inlet 52 to outlet 54.

Ramped portion 75 aids in the insertion of pin 38 into aperture 74. As pin 38 initially moves into aperture 74, ramped portion 75 engages ball 72 and begins moving it downwardly against the force of spring 68.

Figure 5:
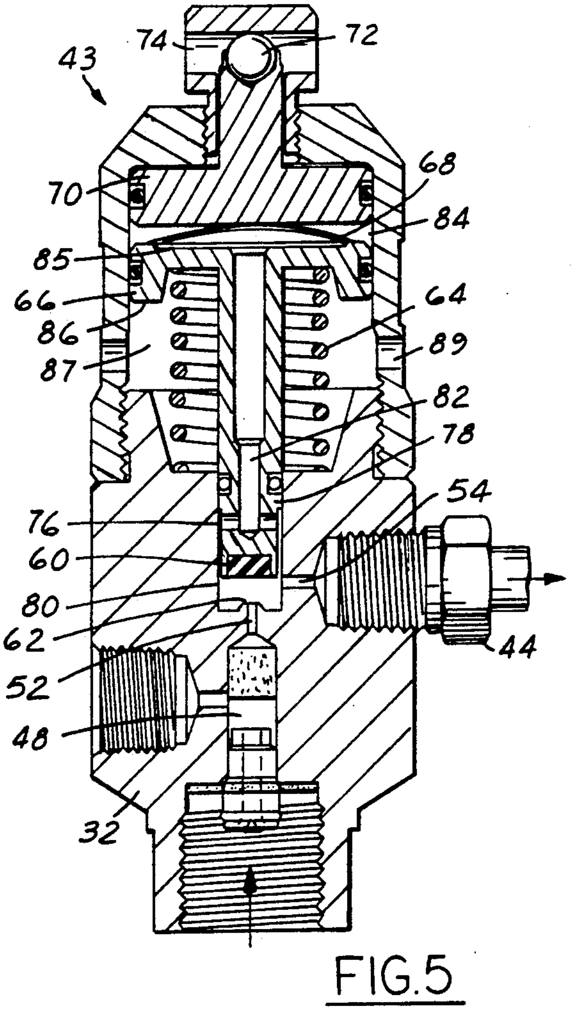
FIG. 5 is a view similar to FIG. 4, but showing the system in its flow-permitting condition.

Valve body 32 is illustrated in FIG. 5 in use position 43. Pin 38 has been removed, enabling spring 68 to displace shut-off piston 70 upwardly, away from regulator piston 66, such that ball 72 is received in aperture 74. Similarly, spring 64 can then displace regulator piston 66 upwardly such that valve seal 60 is removed from valve seat 62, and oxygen flows from inlet 52 to outlet 54.

Once oxygen flow has been actuated from inlet 52 to outlet 54, regulator piston 66 begins to regulate the pressure of oxygen supplied to line 56. Radial clearance passage 76 is formed at a lower extent 78 of regulator piston 66 to allow flow of oxygen between lower extent 78 and the inner periphery of chamber 80. Oxygen flows from radial clearance passage 76, into passage 82, and upwardly through regulator piston 66 to regulator chamber 84. A first face 85 of regulator piston 66 faces regulator chamber 84 and an opposed face 86 faces chamber 87, which is vented to atmosphere at 89.

The regulator function of shut-off pressure regulator valve 58 is known in the art, and thus will only be briefly described. As oxygen is supplied from inlet 52 to outlet 54, it also passes upwardly into regulator chamber 84. The pressure of the oxygen in regulator chamber 84 acts against first face 85 to bias regulator piston 66 downwardly against the force of spring 64. If the pressure within regulator chamber 84 becomes so great that is overcomes spring 64, regulator piston moves downwardly and valve seal 60 approaches valve seat 62 to restrict or block flow of oxygen from inlet 52 to outlet 54. In this way, the pressure of oxygen supplied to oxygen tube 34 is regulated, and overly great pressures are prevented from reaching an oxygen mask connected to oxygen tube 34. By controlling the size of face 85, and the spring force of spring 64, a maximum pressure can be selected.

It may be possible to move ring 40 vertically upwardly and remove it from hook 42, such that system 21 can be removed from bracket 22 without allowing flow of oxygen from tank 32 to oxygen tube 34. This could prove valuable if it becomes necessary to transport system 21 to a remote location. As an example, if system 21 is stored in a home and is required at a remote location, such as in a field adjacent to the home, an operator merely moves ring 40 upwardly off hook 42 and transports system 21 to the remote location. Ring 40 may then be pulled to remove pin 38 from valve body 32.

Figure 6:
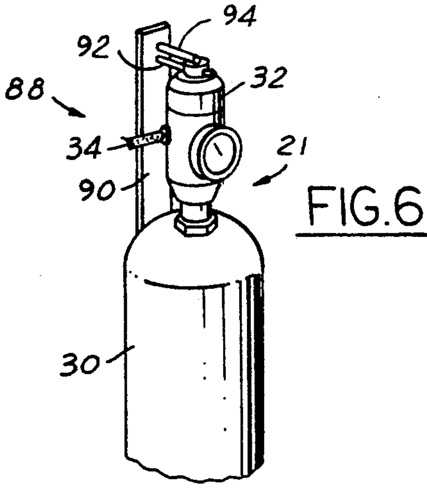
FIG. 6 is a view similar to FIG. 1, but showing a second embodiment of the present invention.

A most preferred embodiment of oxygen supply system 21 is illustrated in storage position 88 in FIG. 6. Bracket 90 includes integral pin 92, which may have a ramped portion similar to portion 75 on pin 38, and extends through aperture 74 to bias ball 72 downwardly. A top guide 94 maintains the stability of oxygen tank 30 and valve body 32 when in storage position 88. Bracket 90 also includes a clip and bottom support similar to features 26 and 28 of bracket 22.

Figure 7:
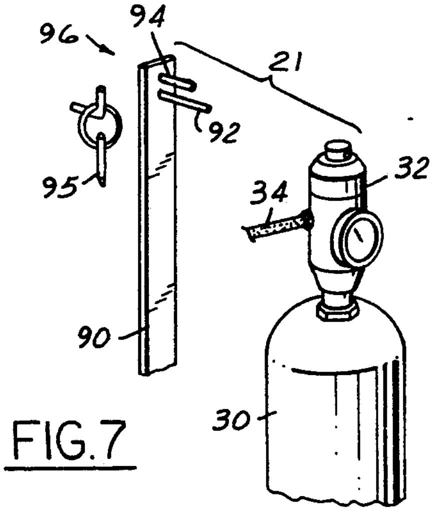
FIG. 7 is a view similar to FIG. 6, but showing the second embodiment in its use position.

FIG. 7 shows the preferred embodiment having been moved to use position 96. When oxygen tank 30 and valve body 32 are removed from bracket 90, pin 92 is removed from aperture 74, and ball 72 moves upwardly, actuating flow of oxygen from inlet 52 to outlet 54.

As a further alternative, a second pin 95, that may be similar to ring 40 and pin 38, may be kept in a position adjacent to bracket 90. If it is desired to transport a system using bracket 90 to a remote location, oxygen tank 30 and valve body 32 are removed, and the second pin is inserted into aperture 74. Although some oxygen will escape before the second pin can be inserted, the loss should be minimal. Emergency oxygen supply system 21 can then be transported to the remote location, where the second pin can be removed.

The method of the present invention will now be explained. An emergency oxygen supply system 21 is mounted on a bracket in a storage position. When mounted in the storage position, a pin maintains valve 58 in a position blocking flow from an oxygen inlet 52 to an outlet 54 so that no oxygen flows from oxygen tank 30 to oxygen tube 34. When an emergency supply of oxygen is necessary, oxygen tank 30 and valve body 32 are removed from the bracket and the pin is automatically removed from valve body 32. Valve 58 moves to a position allowing flow from oxygen inlet 52 to outlet 54, and oxygen is supplied from oxygen tank 30 to oxygen tube 34.

If the first embodiment bracket 22 is utilized, ring 40 may be moved upwardly off of hook 42 to allow emergency oxygen supply system 21 to be transported to a remote location. If the second embodiment bracket 90 is utilized, second pin 95 may be maintained near bracket 90 and inserted into aperture 74 to allow emergency oxygen supply system 21 to be transported to the remote location.

Although brackets 22 and 90 are shown mounted upon wall 24, it should be understood that any other storage position would come within the teachings of this invention. The bracket could be of any configuration, as long as it is used to store a pressurized tank. Also, gases other than oxygen may be stored and actuated according to the teachings of this invention.

The oxygen mask is not illustrated in the disclosed embodiments and forms no part of this invention. The mask would preferably be maintained in an enclosed environment to prevent contamination of the mask and be automatically removable from the enclosure when tank 30 and valve body 32 are removed from the bracket. Pin 92 may be provided with an adjustment means, and may also be used without top guide 94, so that it may pivot vertically with respect to bracket 90 to be quickly aligned with aperture 74.

Although preferred embodiments of the present invention have been disclosed, a worker of ordinary skill in the art would realize that certain modifications would be within the scope of this invention and thus the following claims should be studied in order to determine the true scope and content of the present invention.

We claim:

1. An oxygen supply system comprising:
an oxygen tank containing pressurized oxygen;
a bracket for mounting said tank in a storage position;
said bracket including a pin element, means mounting said pin element such that said pin element normally remains with said bracket;
a valve body having an inlet connected to said tank, an outlet leading to an oxygen tube, and a valve controlling flow between said inlet and said outlet, means in said valve body to receive said pin element when said tank is mounted on said bracket, said pin element when received in said valve body blocking movement of said valve from a closed position to an open position;
said tank and said valve body being removable as a unit from said bracket, said pin element remaining with said bracket thereby enabling said valve to be moved from position blocking flow to a position permitting flow, such that oxygen can flow from said inlet to said outlet.

2. An oxygen supply system as recited in claim 1, wherein said valve comprises a valve seal at a first end, said valve seal being engageable with a valve seat in said valve body, spring means biasing said valve and said valve seal away from said valve seat, said bracket portion contacting a second end, and forcing said valve against said spring means to maintain said valve seal in contact with said valve seat, blocking flow from said inlet to said outlet.

3. An oxygen supply system as recited in claim 2, wherein said valve also regulates the pressure of oxygen supplied to said outlet.

4. An oxygen supply system as recited in claim 3, wherein said valve comprises a pair of pistons, a first of said pair being a regulator piston formed with said valve seal, and said spring means including first spring means forcing said regulator piston away from said valve seat, a second of said pair being a shut-off piston mounted intermediate said regulator piston and said aperture, a second spring means disposed intermediate said regulator piston and said shut-off piston, said bracket portion forcing said shut-off piston against said second spring means such that upon removal of said tank and said valve body from said bracket, said second spring means moves said shut-off piston upwardly into said aperture away from said regulator piston, and defines a fluid chamber intermediate said regulator piston and said shut-off piston.

5. An oxygen supply system as recited in claim 4, wherein oxygen is communicated into said fluid chamber from said inlet and acts against the force of said first spring means such that said regulator piston regulates the pressure of oxygen supplied to said outlet.

6. An oxygen supply system as recited in claim 1, wherein said pin is connected to a ring, and said bracket further includes a hook, said ring being received upon said hook.

7. An oxygen supply system as recited in claim 1, wherein said pin is formed integrally with said bracket.

8. An oxygen supply system as recited in claim 7, wherein a second pin is maintained in the vicinity of said bracket, such that said second pin may be inserted into said aperture when said tank and said valve body are removed from said bracket.

9. An oxygen supply system as recited in claim 1, wherein said pin has a ramped portion at an end which initially enters said aperture, said valve has a ball member normally engaged with said pin at one end, said ramped portion forcing said ball downwardly against said spring means as said pin is guided into said aperture.

10. An oxygen supply system as recited in claim 1, wherein said bracket is mounted on a wall.

11. An oxygen supply system as recited in claim 1, wherein said bracket supports said tank at both bottom and central locations.

12. An oxygen supply system comprising:

an oxygen tank containing pressurized oxygen;

a valve body having an inlet connected to said tank and an outlet leading to an oxygen tube, a valve received within said valve body for controlling flow between said inlet and said outlet, a removable pin maintaining said valve in a position blocking flow from said inlet to said outlet; and said valve also regulating the pressure of oxygen supplied to said outlet when said pin is removed;

said valve comprising a valve seal at a first end, said valve seal being engageable with a valve seat in said valve body, spring means biasing said valve and said valve seal away from said valve seat, said pin forcing said valve against said spring means to maintain said valve seal in contact with said valve seat blocking flow from said inlet to said outlet; and said valve comprising a pair of pistons, a first of said pair being a regulator piston formed with said valve seal, said spring means including first spring means forcing said regulator piston away from said valve seat, a second of said pair being a shut-off piston mounted intermediate said regulator piston and said aperture, a second spring means disposed intermediate said regulator piston and said shut-off piston, said pin forcing said shut-off piston against said second spring means such that upon removal of said pin, said second spring means moves said shut-off valve upwardly into said aperture away from said regulator piston and defines a fluid chamber intermediate said regulator piston and said shut-off piston.

13. An oxygen supply system as recited in claim 12, wherein oxygen is communicated into said fluid chamber from said inlet and acts against the force of said first spring means such that said regulator piston regulates the pressure of oxygen supplied to said outlet.

14. A method of supplying emergency oxygen to a user comprising the steps of:

providing an oxygen tank having a valve body which contains a valve that controls flow from an inlet to an outlet in said valve body;

providing a mounting bracket having a first blocking portion;

mounting said tank and said valve body as a unit on said bracket;

engaging said first blocking portion in said valve body so as to prevent flow of oxygen from said inlet to said outlet;

removing said tank and said valve body as a unit from said mounting bracket;

disengaging said first blocking portion from said valve body, and initiating flow of oxygen from said inlet to said outlet;

providing a second blocking portion in the vicinity of said bracket;

removably inserting said second blocking portion into said valve body when said tank and valve body are removed form said bracket and said first blocking portion so as to stop flow of oxygen from said inlet and said outlet; and removing said second blocking portion from said valve body and supplying oxygen to a user when desired.

* * * * *